United States Patent [19]

Mueller et al.

[11] Patent Number: 4,803,294

[45] Date of Patent: Feb. 7, 1989

[54] PROCESS AND INTERMEDIATES FOR THE PREPARATION OF HALOGENATED PROTEASE INHIBITORS

[75] Inventors: Richard A. Mueller, Glencoe; Richard A. Partis, Evanston, both of Ill.

[73] Assignee: G. D. Searle & Co., Chicago, Ill.

[21] Appl. No.: 114,186

[22] Filed: Oct. 29, 1987

[51] Int. Cl.$^4$ .............................................. C07C 69/76
[52] U.S. Cl. ................................ 560/54; 260/544 D; 260/410.9 R; 560/83; 562/459; 562/474; 562/480
[58] Field of Search .......................................... 560/54

[56] References Cited

U.S. PATENT DOCUMENTS 4,469,885 2/1985 Mueller et al. .
4,501,895 9/1984 Mueller et al. .

*Primary Examiner*—Paul J. Killos
*Attorney, Agent, or Firm*—Mary Jo Kanady; Paul D. Matukaitis

[57] ABSTRACT

This invention relates to novel intermediate compounds which are useful for producing the halogenated protease inhibitors that are the subject matter of U.S. Pat. No. 4,469,885. In particular, the invention relates to novel methods and intermediates for making said protease inhibitors, the intermediate compounds being of the formula:

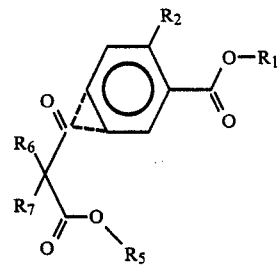

wherein $R_1$ is:
(a) straight or branched chain lower alkyl having 1–6 carbon atoms; or
(b) H;

wherein $R_6$ is:
(a) straight or branched chain higher alkyl having 13–25 carbon atoms; or
(b) straight or branched chain higher alkenyl having 13–25 carbon atoms;

wherein $R_5$ is:
(a) straight or branched chain lower alkyl having 1–6 carbon atoms; or
(b) benzyl;

wherein $R_7$ is:
(a) straight or branched chain lower alkyl having 1–6 carbon atoms; or
(b) H;

wherein $R_2$ is:
(a) —Cl, —Br, or —I; or
(b) —CF$_3$.

5 Claims, No Drawings

PROCESS AND INTERMEDIATES FOR THE PREPARATION OF HALOGENATED PROTEASE INHIBITORS

BACKGROUND OF THE INVENTION

This invention, in its broadest aspect, relates to enzyme inhibitors. In particular, it relates to a method for preparing compounds of Formula I which are useful in preventing or treating disease states caused by the action of proteases and other enzymes on mammalian elastin or other proteins. Thus, the present invention relates to certain compounds useful in preventing or treating disease states caused by the degradative action of elastases or cathepsin G, such as pulmonary emphysema, arthritis, and artherosclerosis. In particular, the present invention relates to novel intermediates of Formula II for an improved method for preparing the compounds of Formula I.

Elastin is the functional protein component of elastic fiber tissues, a component of connective tissue. Elastic tissue is relatively rich in elastin and has a distinct rubber-like property. Most specifically, the ligamentum nuchae and the vocal cords, the vertebral ligamenta flava, the aorta, and the pulmonary arteries of some mammals are considered elastic tissues. Elastic cartilaginous tissues such as those present in the ear and epiglottis are a specialized form of elastic tissue. Lung, bronchi and skin also contain elastin and are considered elastic tissue. Sandberg, et al., *New England Journal of Medicine*, Mar. 5, 1981, 566–579.

Elastase is an elastinolytic enzyme which causes degradation and fragmentation of elastic fibers by its catalytic activity against elastin. Elastases orginate from a number of sources and can be found in microorganisms, snake venoms and a number of mammalian cells and tissues including pancreas, polymorphonuclear leukocytes, and macrophages. In a normally functioning mammal, elastase is required for turnover of connective tissue, damaged cells and the digestion of certain invading bacteria. Elastase activity is stimulated by Cathepsin G which like elastase is also released by polymorphonuclear luckocytes. Boudier, et al., *The Journal of Biological Chemistry*, 256:10256–10258, (1981).

Natural protease inhibitors are, for example, alpha-1-protease inhibitor (alpha-1-PI, alpha-1-antitrypsin) and alpha-1-antichymotrypsin. A deficiency of alpha-1-antitrypsin results in the proteolysis (degradation) of elastin, proteoglycans, fibronectin, collagen and basement membrane, producing and leading to connective tissue diseases and inflammation. A deficiency of effective alpha-1-PI can be generated either by a genetic defect, by the uncontrolled oxidation of alpha-1-antitrypsin, by natural oxidants, or by chemical oxidants (e.g., cigarette smoke). The combination of alpha-1-PI deficiency and oxidation increases the inflammatory burden.

The protein degradation products of elastase are often biologically active. For example, the $C_{5a}$ component of complement is a potent chemotactic agent for neutrophils and perhaps also for metastatic tumor cells. The $C_{5a}$ component of complement is produced by the protease action of elastase on $C_5$ component of complement. The release of $C_{5a}$ leads to further protease release, oxidant release, and the biosynthesis of products from the arachiodonic acid cascade such as $PGE_2$, $LTB_4$, $LTD_4$, diHETES, triHETES, etc. (Weiss, et al., *Journal of Clinical Investigation*, 73:1297–1303 (1984), Schalkwijk, et al., *British Journal of Experimental Pathology*, 68:81–88, (1987), Kleesick, et al., *Rheumatology International*, 6:161–169, (1986), Campbell, E. J., *American Review of Respiratory Diseases*, 134:435–437 (1986)) as well as oxidative inactivation of alpha-1-PI. Elastin fragments are chemotactic, antigenic and effect the ion flux in smooth muscle cells, fibroblasts and mononuclear cells. Jacob, et al., *Proceedings of The National Acadamy of Sciences* U.S.A., 84:995–999 (1987).

Elastase is also important for the control of the serpins. Serpins are serine protease inhibitors that control the triggering of inflammatory cascades such as coagulation, kinin release, fibrinolysis and complement activation. Members of this class of potent control biochemicals include alpha-1-antitrypsin, alpha-1-antichymotrypsin, antithrombin III, C1 inhibitor, alpha-2-antiplasmin, Heparin cofactor II, PC inhibitor, PA inhibitor and angiotensinogen. The importance of these materials in inflammatory, cardiovascular and immunological disease states is well known to those skilled in the art. Elastase inactivates these proteins and/or causes their clevage to other active materials. Carrell, *Journal of Clinical Investigation*, 78:1427–1431 (1986). For example, angiotensinogen (inactive) is converted directly to angiotensin II (active) by elastase, thus bypassing the angiotensin converting enzyme blood pressure control system. This invention in particular relates to the class of proteases known as the serine proteases.

Excessive elastin degradation by elastase has been associated with pulmonary emphysema, adult respiratory-distress syndrome, chronic obstructive lung disease, arthritis, atherosclerosis, certain skin diseases, and certain inflammatory processes leading to localized protein breakdown. Werb, et al., *Journal of Investigative Dermatology*, 79:154S-159S, (1982); Rinaldo, et al., *New England Journal of Medicine*, 306:900–909, (1982). Therefore, by inhibiting elastase, it is possible to mediate, eliminate or treat a wide variety of disease conditions.

A number of inhibitors of elastase are known. Peptide chloromethyl ketones have been shown to be irreversible inhibitors of elastase. But difficulties must be considered when the in vivo use of peptide chloromethyl ketones is contemplated. These compounds are electrophiles and can react with good in vivo nucleophiles such as the thiol groups of glutathione and various proteins. During any long term treatment with these inhibitors, such non-specific alkylation could lead to the introduction of new antigenetic determinants and thus an immune response and/or could behave similarly to the known nitrogen mustards, etc.

Peptides containing aza-amino acid residues (aza-peptides) are another class of inhibitors. The effectiveness of aza-peptides as elastase inhibitors depends on the rate of acylation, which in most cases is instantaneous, and also on the rate of deacylation. As such, these compounds, while useful tools in studying the in vitro properties of elastase, are still largely unsuitable for in vivo use.

Unlike aza-peptides or peptide chloromethyl ketones, the compounds of this invention are chemically stable, orally active inhibitors of elastase and cathepsin G. They can be formulated or administered as single active moietys or in combination with, for example, cyclooxygenase inhibitors, lipoxygenase inhibitors, antioxidants and the like to provide effective treatment of elastase/cathepsin G/oxidation related diseases as defined by those skilled in the art.

Enzyme inhibitors of Formula I and their advantages are disclosed in U.S. Pat. No. 4,469,885, issued to Mueller, et al. on Sept. 4, 1984 and U.S. Pat. No. 4,501,895, issued to Mueller, et al. on Feb. 26, 1985. Heretofore, the preparation of these halogenated protease inhibitors utilized many synthetic steps because the most preferred starting materials were not commercially available in quantity and carried a high cost. Moreover, the preparation also required two chromatographic purification steps. Chromatography is expensive when carried out on a large scale. Furthermore, the synthesis of the protease inhibitors of Formula I, via for example, aromatic diazo intermediates, could be dangerous on a large scale, due to the potential for explosive decomposition.

In its broadest scope, the present process allows the regiospecific synthesis of benzoylacetic acid esters of Formula II that are readily converted to the elastase inhibitors of Formula Ia (a subgroup of Formula I). By regiospecific (regioselective) is meant that condensation of an alkylcarboxylic acid ester with a substituted aryldicarboxylic acid mono or diester occurs at the less hindered position.

SUMMARY OF THE INVENTION

This invention relates to novel intermediates for use in preparing the protease inhibitors that are the subject matter of U.S. Pat. No. 4,469,885, said protease inhibitors being of the formula:

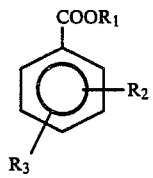

wherein $R_1$ is:
(a) hydrogen; or
(b) alkyl of 1 to 6 carbon atoms, inclusive;
wherein $R_2$ is:
(a) —Cl, —Br, or I; or
(b) trifluoromethyl
wherein $R_3$ is:
(a) —C(O)R$_4$;
(b) —CH(OH)R$_4$;
(c) —CH$_2$R$_4$; or
(d) —CH=CHR$_4$;
wherein $R_4$ is alkyl of 13 to 25 carbon atoms inclusive as well as their branched chain isomers.

More specifically the present invention relates to novel intermediates for use in preparing a subgroup of the protease inhibitors of Formula I said subgroup being of the formula:

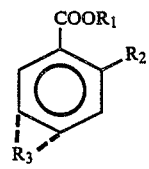

wherein $R_1$, $R_2$, $R_3$ and $R_4$ are as defined for Formula I.

In particular, the present invention encompasses novel intermediate compounds which are useful for preparing the protease inhibitors of Formula Ia, said novel intermediate compounds being of the formula:

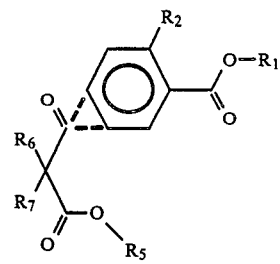

wherein $R_1$ is:
(a) straight or branched chain lower alkyl having 1–6 carbon atoms; or
(b) H;
wherein $R_6$ is:
(a) straight or branched chain higher alkyl having 13–25 carbon atoms; or
(b) straight or branched chain higher alkenyl having 13–25 carbon atoms;
wherein $R_5$ is:
(a) straight or branched chain lower alkyl having 1–6 carbon atoms; or
(b) benzyl;
wherein $R_7$ is:
(a) straight or branched chain lower alkyl having 1–6 carbon atoms; or
(b) hydrogen; and
wherein $R_2$ is:
(a) —Cl, —Br, or —I; or
(b) —CF$_3$.

As disclosed in U.S. Pat. Nos. 4,469,885 and 4,501,895, the enzyme inhibitors of Formula I and their mode of synthesis are known. The present invention describes an improved method for making some of the enzyme inhibitors of Formula I, particularly those inhibitors encompassed by Formula Ia.

It is an object of the present invention to minimize the number of steps necessary to synthesize the enzyme inhibitors of Formula Ia.

It is a further object of the invention to enhance the minimum yield of protease inhibitors obtained during the synthesis thereof. Yet another object of the present invention is to provide a synthesis for enzyme inhibitors of Formula Ia that does not require chromatographic purification steps.

Still another object of the present invention is to provide a facile synthesis of enzyme inhibitors of Formula Ia that uses pure, commercially available reagents and that is easily implemented on a large scale.

DETAILED DESCRIPTION

This invention relates to a novel process for producing a subgroup of the halogenated protease inhibitors of U.S. Pat. No. 4,469,885, said subgroup of inhibitors being represented by Formula Ia. In particular, this invention relates to intermediate compounds in the process which are represented by Formula II. This process is presented in Chart A, wherein $R_1$, $R_2$, $R_5$, $R_6$, and $R_7$ are defined as for Formul The process uses readily available starting materials, halo-xylenes, wherein by halo- is meant mono- chloro, bromo, iodo, or trifluoromethyl attached directly to the aromatic ring. The halo-xylene is oxidized to its corresponding dicarboxy-halobenzene by oxygen and Co(II) acetate .4H$_2$O dissolved in glacial acetic acid in the presence of HBr. The preferred dicarboxy-halobenzene species are 1,4-dicarboxy-2-halobenzene XI and 1,3-dicarboxy-4-halobenzene.

By way of illustration (Chart A), 1,4-dicarboxy-2-halobenzene (XI) can be converted directly to a diester (XIII) by reaction with a lower alkyl alcohol (R$_1$OH). By lower alkyl is herein meant straight or branched chain alkyl having 1-6 carbon atoms. Alternatively, the halo-dicarboxylic acid (XI) can be initially converted into a halo-diacyclchloride (XII), such as by reaction with oxalyl chloride. Subsequent reaction of XII with a lower alkyl alcohol would also produce the halo-diester (XIII). By varying R$_1$ in the lower alkyl alcohol, the necessary diversity of R$_1$ in the claimed intermediate XVI can be achieved.

The monoacid-monoester (XIV) can be achieved either by hydrolysis of one of the two ester groups of XIII, or by refluxing the diacid (XI) in the presence of concentrated sulfuric acid (H$_2$SO$_4$) using the corresponding lower alkyl alcohol (R$_1$OH) as the solvent. Acid hydrolysis preferentially occurs on the ester group that is ortho to the halo-group defined above. Acid catalyzed synthesis preferentially occurs at the unhindered carboxylic acid, producing a halobenzene-monoester-mono-carboxylic acid (XIV). Alkaline hydrolysis of XIII, such as by aqueous potassium hydroxide, KOH, (not shown), produces mixture of mono-carboxylic acids wherein the halo-group is either ortho or meta to the hydrolyzed ester (carboxylic acid). Selective crystallization provides the ortho and meta isomers; the undesired isomer can be recycled.

The intermediate compounds claimed in the present invention, represented generally by Formula II, and more specifically by Compound XVI in Chart A, are made be condensing either the halo-diester (XIII) or the halo-mono-ester-mono-carboxylic acid (XIV) with the enolate anion of an ester (XV) in the presence of a moderately strong, non-nucleophilic or sterically hindered base, preferably the product obtained from the treatment of diisopropylamine with n-butyllithium (LDA), in an aprotic solvent, preferably tetrahydrofuran (THF). By a non-nucleophilic or sterically hindered base is meant a base such as sodium hydride, potassium hydride, LDA, lithium cyclohexylisopropylamine, potassium hexamethyldisilazide and the like, which can deprotonate an ester. Representative of such esters is t-butyl octadecanoate, prepared according to the procedure in *J. Am. Chem. Soc.*, 81, 3444 (1959). Preferred esters are

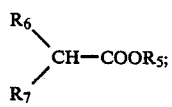

wherein R$_6$ is either straight or branched chain higher alkyl having from about 13 to about 25 carbon atoms, or is straight or branched chain higher alkenyl having from about 13 to about 25 carbon atoms; wherein R$_7$ is straight or branched chain lower alkyl having from about 1 to 6 carbon atoms or hydrogen; and wherein R$_5$ is straight or branched chain lower alkyl having 1-6 carbon atoms or benzyl. In the above ester, R$_5$ is preferably a sterically hindered group, most preferably t-butyl. When R$_5$ is a sterically hindered group, self condensation is prevented and regiospecificity of condensation with an unsymmetrical aromatic diester or monoacid-monoester is increased.

Hydrolysis of the β-keto-ester (XVI) and its subsequent decarboxylation is achieved in a single step by CF$_3$COOH to produce one of the series of compounds (XVII) claimed in U.S. Pat. No. 4,469,885. Alkaline hydrolysis of this halo-ester series of compounds (XVII) produces the halo-carboxylic acid series (XVIII). Further selective reaction of the keto-group, preferably with NaBH$_4$ or other reducing agents, produces the hydroxyl series compounds (XIX).

By varying the starting halo-dicarboxylic acid from the 1,4-dicarboxy-2-halobenzene of formula XI to 1,3-dicarboxy-4-halobenzene, one also obtains the corresponding regiospecific condensation product, wherein condensation occurs on the sterically unhindered carboxyl species, i.e., the carboxyl species having no halo substituent ortho to it.

By varying R$_1$, R$_2$, R$_5$, R$_6$ and R$_7$ as disclosed above, the necessary variations can be achieved to produce the intermediate compounds claimed in this invention.

The following examples are given by way of illustration only and in no way should be construed as limiting the invention in spirit or in scope, as many modifications in materials and methods will be apparent from this disclosure to those skilled in the art.

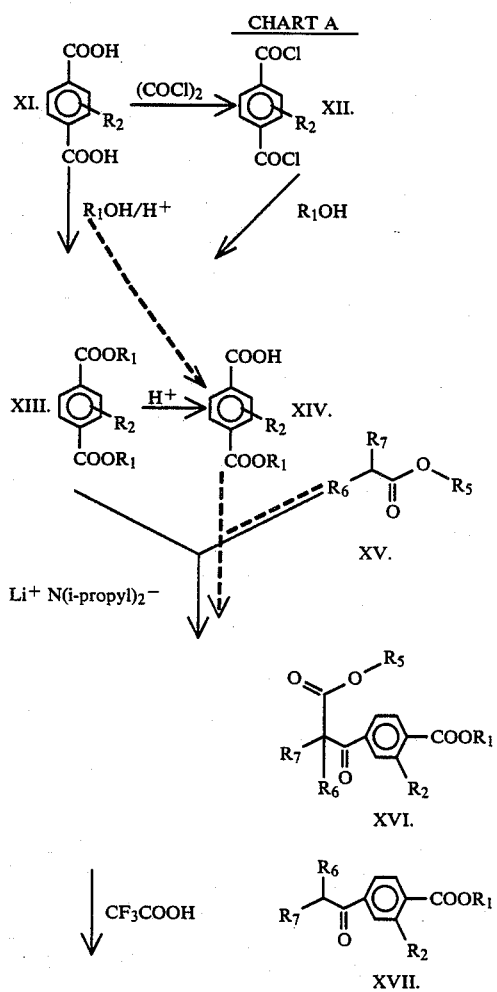

-continued
CHART A

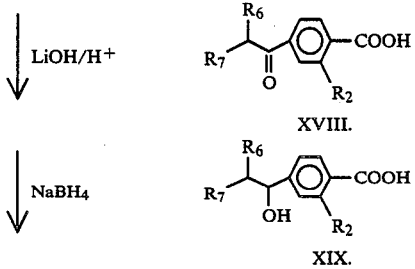

DESCRIPTION OF THE PREFERRED EMBODIMENT

EXAMPLE 1

2-chloro-1,4-benzenedicarboxylic acid

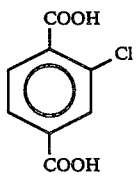

Cobalt(II) acetate .4H$_2$O (12.5 g) was dissolved with stirring in 250 ml of glacial acetic acid followed by the addition of 13.5 g of 48% hydrogen bromide in acetic acid. When a deep purple/blue color color persisted, 35.25 g of 2-chloro-p-xylene was added. The mixture was heated for about 6 hours with the continuous addition of oxygen gas at such a rate that the sintered glass delivery tube did not become blocked to the passage of the gas. The reaction mixture was cooled to room temperature (R.T.) and then filtered. The crystals of the product were washed three times with water (H$_2$O) and allowed to dry in air. The product (33.7 g) after drying was characterized by its combustion analysis, m.p. approx. 313° C.

Analysis for C$_8$H$_5$ClO$_4$ (M.W.=200.577): Calcd: C, 47.90; H, 2.51; Cl, 17.68. Found: C, 47.81; H, 2.32; Cl, 17.99.

EXAMPLE 2 dimethyl 2-chloro-1,4-benezenedicarboxylate

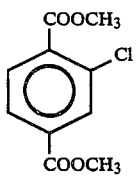

To 15.3 g of product from Example 1 suspended in 150 ml of methanol was added 1 ml of concentrated sulfuric acid. The reaction mixture was heated at reflux for two days, cooled to R.T. and anhydrous sodium carbonate (Na$_2$CO$_3$) was added with stirring. The methanol solution was filtered and about 50 ml of water was added. The crystalline product (14.8 g) which formed, was filtered and dried. The melting point of the crystalline product was approximately 56°-60° C.

Analysis for C$_{10}$H$_9$O$_4$Cl (M.W.=228.629): Calcd: C, 52.53; H, 3.97; Cl, 15.51. Found: C, 52.49; H, 3.84; Cl, 15.38.

EXAMPLE 3

2-chloro-1,4-benzenedicarbonyl dichloride

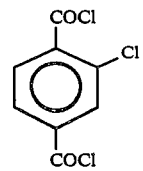

To 2.0 g of product from Example 1 suspended in 125 ml of benzene, was added 0.54 ml of oxalyl chloride. The reaction mixture was refluxed overnight and an additional 0.7 ml of oxalyl chloride was added with continued refluxing. After 8 hours, an additional 1.0 ml of oxalyl chloride was added. Upon refluxing an additional 18 hours, the solvent was removed using a rotary evaporator. Benzene (50 ml) was then added and the evaporation repeated to give the product as a light yellow oil.

EXAMPLE 4

Mixture of:
2-chloro-1,4-benzenedicarboxylic acid, 1-methyl ester, monopotassium salt (A)
2-chloro-1,4-benzenedicarboxylic acid, 4-methyl ester, monopotassium salt (B)

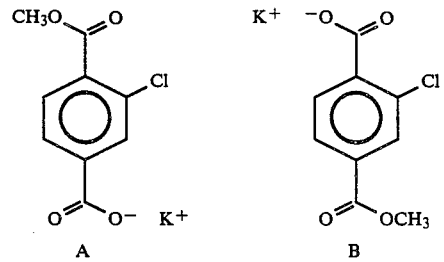

To 0.5 g of product from Example 2 dissolved in 10 ml of toluene was added 0.85 equivalent of 1N KOH. The reaction mixture was stirred at room temperature and then warmed to about 60° C. After two hours, the reaction was cooled to room temperature and the precipitate was filtered, washed two times with toluene and dried at 50° C. at 1.5 mm for two hours. The product was identified by its PMR spectrum, m.p. about 262° C.

EXAMPLE 5

Mixture of:
1-methyl 2-chloro-1,4-benzenedicarboxylate (A)
4-methyl 2-chloro-1,4-benzenedicarboxylate (B)

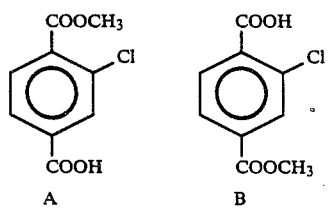

Acidification of product from Example 4 with 10% hydrochloric acid gives the titled acids.

EXAMPLE 6

1,1-dimethylethyl octadecanoate

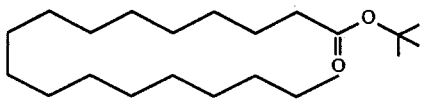

The product of this example was synthesized by the method disclosed in *J. Am. Chem. Soc.*, 81, 3444 (1959), m.p. 35° C.

Analysis for $C_{22}H_{44}O_2$ (M.W.=340.49): Calcd: C, 77.59; H, 13.02. Found: C, 77.98; H, 13.22.

EXAMPLE 7 bis(1-methylethyl) 2-chloro-1,4-benzenedicarboxylate

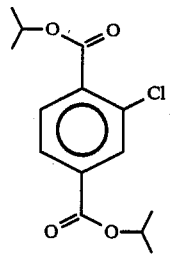

To 2.0 g of product from Example 1 suspended in 25 ml of isopropyl alcohol was added 0.3 ml of conc. $H_2SO_4$ and the reaction mixture heated at reflux for about 18 hours. Conc. $H_2SO_4$ (5 drops) was then added and heating continued for an additional 24 hours. The reaction mixture was cooled to room temperature. The solvent was removed and the residue treated with 50 ml of saturated sodium bicarbonate solution and 50 ml of ethyl acetate. The organic phase was dried over sodium sulfate and the solvent removed under nitrogen. Dissolution in pentane followed by removal of the solvent gave the above product.

Analysis for $C_{14}H_{17}O_4Cl$ (M.W.=284.73): Calcd: C, 59.05; H, 6.02; Cl, 12.45. Found: C, 59.30; H, 5.87; Cl, 12.33.

EXAMPLE 8

Mixture of:
2-chloro-1,4-benzenedicarboxylic acid, 1-(1,1-dimethylethyl) ester (A) and
2-chloro-1,4-benzenedicarboxylic acid, 4-(1,1-dimethylethyl) ester (B)

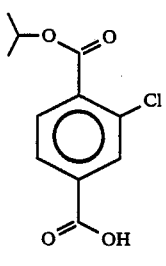 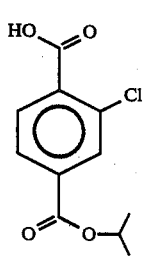

A                B

The sodium bicarbonate extract from Example 7 was acidified with 10% hydrochloric acid and extracted with ethyl acetate. The organic extracts were dried over sodium sulfate, filtered and the solvent removed on a rotary evaporator. The residue was dissolved in hexane and placed in a refrigerator. When cooled, the white solid was filtered and chromatographed on silica gel eluting with 20% ethyl acetate/hexane/1% acetic acid. The solid obtained was recrystallized from ethyl ether/hexane, filtered and dried at room temperature under vacuum.

Analysis for $C_{11}H_{11}O_4Cl$ (M.W.=242.66): Calcd: C, 54.45; H, 4.57; Cl, 14.61. Found: C, 54.05; H, 4.41; Cl, 14.47.

EXAMPLE 9

1,1-dimethylethyl 3-chloro-α-hexadecyl-4-(1-methylethoxycarbonyl)-β-oxobenzenepropanoate

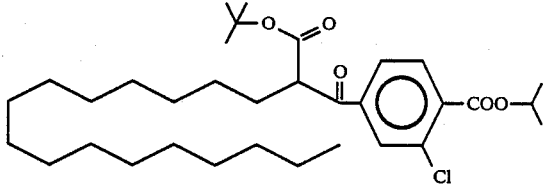

The product from Example 6 (1.99 g) in 10 ml of tetrahydrofuran (THF) was added dropwise under argon to a cooled (about −75° C.) solution of diisopropylamino lithium (from n-butyllithium and diisopropylamine) with stirring. After stirring for three hours, the temperature was raised to about −20° C. and then cooled to about −55° C. Then, 1.66 g of the product from Example 7, dissolved in 10 ml of THF was added dropwise over about 20 minutes. The reaction mixture was allowed to warm to room temperature with constant stirring over about 18 hours. The reaction mixture was diluted with 5 ml of water and 5 ml of 10% hydrochloric acid. The organic layer was separated and dried ($Na_2SO_4$). The residue from removal of the solvent was chromatographed on silica gel eluting with 2% and 5% ethyl acetate/hexane to give a clear oil which can become a solid, m.p. approximately 44° C.

Analysis for $C_{33}H_{53}O_5Cl$ (M.W.=565.23): Calcd: C, 70.12; H, 9.45; Cl, 6.27. Found: C, 70.13; H, 9.28; Cl, 6.17.

EXAMPLE 10

1-methylethyl 2-chloro-4-(1-oxooctadecyl)benzoate

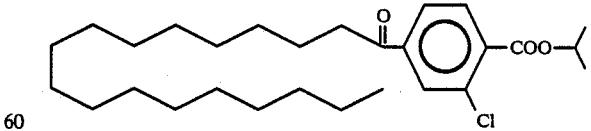

335 mg of product from Example 9 was dissolved in 10 ml of methylene chloride and 10 ml of trifluroacetic acid was added. The reaction mixture was stirred at room temperature for 1.5 hours and added to 20 ml of water. The organic layer was separated and dried over sodium sulfate. The solvent was removed using a rotary evaporator to give 270 mg of the titled product.

EXAMPLE 11

2-chloro-4-(1-oxooctadecyl)benzoic acid

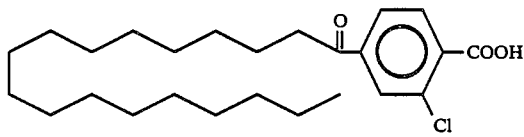

The product from Example 10 (270 mg) was suspended in 10 ml of isopropyl alcohol and warmed. 20 ml of tetrahydrofuran was added. 200 mg of lithium hydroxide monohydrate in 3 ml of water was added followed by an additional 5 ml of water. The reaction mixture was stirred at room temperature for about 20 hours and 20 ml of 10% hydrochloric acid was added. The organic solvents were removed using a rotary evaporator and the residue was extracted with two 50 ml portions of ethyl ether. The ether extracts were combined, dried over sodium sulfate, filtered and the solvent removed under a nitrogen gas stream. The product is a white solid identical with the product disclosed in Example 15 in U.S. Pat. No. 4,469,885.

EXAMPLE 12

2-chloro-4-(1-hydroxyoctadecyl)benzoic acid

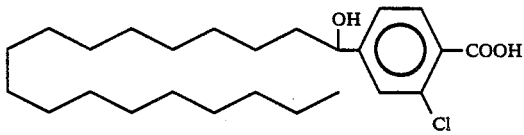

To 159 mg of product from Example 11 suspended in 10 ml of ethyl alcohol at 0° C. was added 13 mg of sodium borohydride. An additional 10 ml of ethyl alcohol was added and the reaction stirred overnight while allowed to warm to room temperature. An additional 40 mg of sodium borohydride was added followed in about 20 hours by 50 ml of ethanol and 100 mg of sodium borohydride. Stirring was continued for 20 hours whereupon 25 ml of water was added, followed by 20 ml of 10% hydrochloric acid. The organic solvent was removed using a rotary evaporator and the aqueous residue extracted with two 50 ml portions of ethyl ether. The organic extracts were combined, washed with water, dried over sodium sulfate, and filtered. The solvent was removed using a rotary evaporator to give a white solid (150 mg). Recrystallization of the solid from methanol/hexane gave 139 mg of product identical with that disclosed in Example 14 of U.S. Pat. No. 4,469,885.

EXAMPLE 13

1,1-dimethylethyl 3-chloro-α-hexadecyl-4-(1-methoxycarbonyl)-β-oxobenzenepropanoate

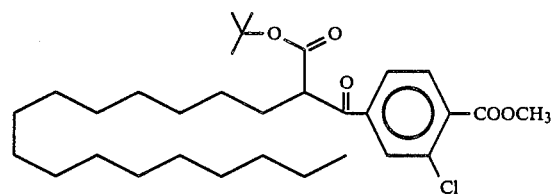

By the method of Example 9 using the product of Example 2 and the product of Example 6, the above was obtained. M.P. approximately 43°–46° C.

Analysis for $C_{31}H_{49}O_5Cl$ (M.W.=537.18): Calcd: C, 69.31; H, 9.19; Cl, 6.60. Found: C, 69.04; H, 9.05; Cl, 6.86.

EXAMPLE 14

Methyl 2-chloro-4-(1-oxooctadecyl)benzoate

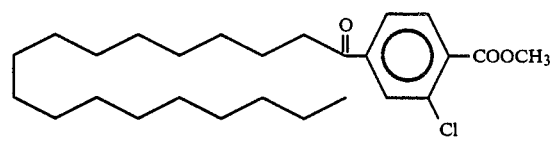

By the method of Example 10, 400 mg of product from Example 13 was treated with 10 ml of trifluroacetic acid in methylene chloride to give 320 mg of the title compound, as disclosed and claimed in U.S. Pat. No. 4,469,885. The product is used in Example 15.

EXAMPLE 15

2-chloro-4-(1-oxooctadecyl)benzoic acid

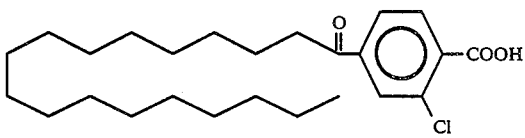

By the method of Example 11, 320 mg of the product of Example 14 was treated with 200 mg of lithium hydroxide monohydrate to give the product of Example 11, the title compound.

EXAMPLE 16

1,1-dimethylethyl 3-chloro-α-hexadecyl-4-carboxy-β-oxobenzenepropanoate

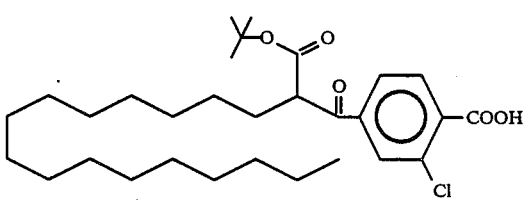

By the method of Example 9 using isopropylcyclohexylamine, n-butyl lithium, 1.44 g of the product from Example 18, and 2.02 g of product from Example 6, the title compound was obtained.

Analysis for $C_{30}H_{47}O_5Cl$ (M.W.=523.133): Calcd: C, 68.87; H, 9.06; Cl, 6.79. Found: C, 68.55; H, 9.01; Cl, 6.86.

EXAMPLE 17

2-chloro-4-(1-oxooctadecyl)benzoic acid

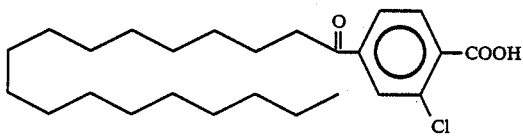

475 mg of product from Example 16 was treated by the method of Example 10 to give the title compound which is identical with the product from Example 11.

EXAMPLE 18

2-chloro-1,4-benzenedicarboxylic acid, 4-(1-methylethyl) ester

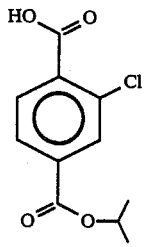

The product from Example 1 (20.85 g), was heated at reflux with 100 ml of isopropyl alcohol and 1.0 ml of concentrated sulfuric acid for 20 hours. The solution was diluted with 200 ml of saturated sodium carbonate solution and 150 ml of water. It was then extracted twice with 250 ml portions of ether. Following acidification with 10% hydrochloric acid, the aqueous phase was extracted three times with 250 ml portions of ether. The ether extracts were combined and the solvent removed under nitrogen to give white crystals. Recrystallization of a portion of the crystals from hexane gave the title compound, m.p. 110°-114° C.

Analysis for $C_{11}H_{11}O_4Cl$ (M.W.=242.66): Calcd. C, 54.45; H, 4.57; Cl, 14.61. Found: C, 54.61; H, 4.53; Cl, 14.73.

EXAMPLE 19 bis(1,1-dimethylethyl) 2-chloro-1,4-benzenedicarboxylate

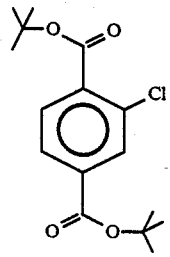

To 24.7 g of product from Example 1 dissolved in 400 ml of tetrahydrofuran was added 31.2 g of oxalyl chloride and the solution stirred at reflux temperature for about 20 hours. An additional 30 ml of oxalyl chloride was added and reflux continued for an additional 24 hours. The solution was cooled and allowed to stir at room temperature for about four days. Following the addition of 15 ml of oxalyl chloride, the solvents were removed under reduced pressure on a rotary evaporator. To the residue was added 200 ml of benzene and the solvent removed by rotary evaporation. The addition of benzene and its removal was again repeated to give the product of Example 3—a diacyl dichloride. The diacyl dichloride was dissolved in 100 ml of tetrahydrofuran (THF) followed by the addition of 100 ml of t-butyl alcohol. The solution was cooled in an ice bath to about 0°-5° C. and 10 ml of pyridine was added. The reaction mixture, now containing pyridine hydrochloride, was stirred at room temperature (R.T.) for about 18 hr. and then refluxed for 4 days. Afterwards, the reaction mixture was cooled to room temperature, filtered, and the solvents removed by rotary evaporation. The resulting oil was dissolved in ether, filtered and extracted sequentially with two 50 ml portions of 1N HCl (hydrochloric acid), 50 ml of 10% sodium carbonate. After drying over magnesium sulfate ($MgSO_4$), the solvent was removed under a stream of nitrogen gas ($N_2$). The resulting oil was chromatographed on silica gel. Elution with ethyl acetate (20%) in hexane gave the titled product.

EXAMPLE 20 bis(1-methylethyl) 2-chloro-1,4-benzenedicarboxylate

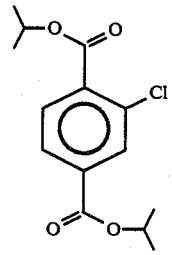

Into 50 ml of isopropyl alcohol was dissolved 2.36 g of the product of Example 3 and 1.38 g of pyridine. The solution was stirred at room temperature (R.T.) for about 56 hr. and then added to about 300 ml of water. The resulting mixture was washed sequentially with three 100 ml portions of 0.5N hydrochloric acid, once with 100 ml of 5% sodium carbonate solution, and once with 100 ml of water. The organic phase was separated and dried ($MgSO_4$). The solvent was then removed under reduced pressure to give 2.5 g of a light yellow oil identical with the product of Example 7.

What is claimed is:

1. A compound of the formula:

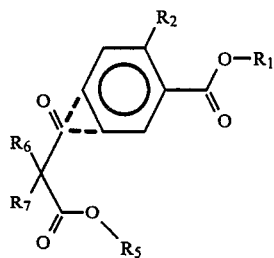

wherein $R_1$ is:
  (a) straight or branched chain lower alkyl having 1-6 carbon atoms; or
  (b) H;
wherein $R_6$ is:
  (a) straight or branched chain higher alkyl having 13-25 carbon atoms; or
  (b) straight or branched chain higher alkenyl having 13-25 carbon atoms;
wherein $R_5$ is:
  (a) straight or branched chain alkyl having 1-6 carbon atoms; or
  (b) benzyl;
wherein $R_7$ is:
  (a) straight or branched chain lower alkyl having 1-6 carbon atoms; or
  (b) H;
wherein $R_2$ is:
  (a) —Cl, —Br, or —I; or
  (b) —$CF_3$.

2. A compound according to claim 1 of the formula:

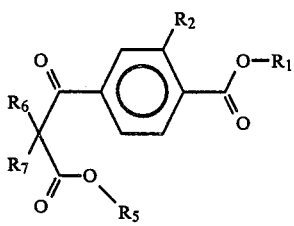

wherein $R^1$ is:
  (a) straight or branched chain lower alkyl having 1-6 carbon atoms; or
  (b) H;
wherein $R_6$ is:
  (a) straight or branched chain higher alkyl having 13-25 carbon atoms; or
  (b) straight or branched chain higher alkenyl having 13-25 carbon atoms;
wherein $R_5$ is:
  (a) straight or branched chain alkyl having 1-6 carbon atoms; or
  (b) benzyl;
wherein $R_7$ is:
  (a) straight or branched chain lower alkyl having 1-6 carbon atoms; or
  (b) H;
wherein $R_2$ is:
  (a) —Cl, —Br, or —I; or
  (b) —$CF_3$.

3. A compound according to claim 2 of the formula:

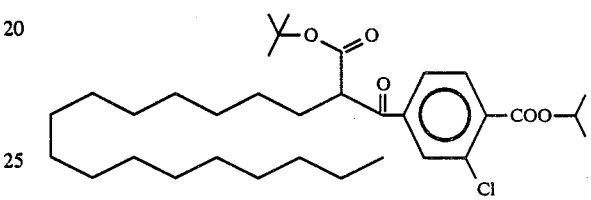

4. A compound according to claim 2 of the formula:

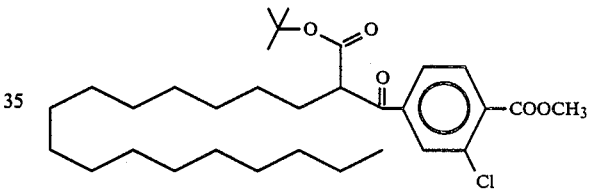

5. A compound according to claim 2 of the formula

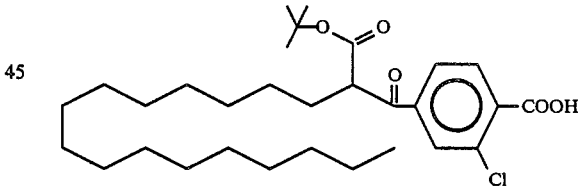

* * * * *

UNITED STATES PATENT AND TRADEMARK OFFICE
CERTIFICATE OF CORRECTION

PATENT NO. : 4,803,294

DATED : Feb. 7, 1989

INVENTOR(S) : Mueller, et al.

It is certified that error appears in the above-identified patent and that said Letters Patent is hereby corrected as shown below:

Column 4, line 64, reading "Formul" should read -- Formula II --.

Signed and Sealed this

Twelfth Day of March, 1991

*Attest:*

HARRY F. MANBECK, JR.

*Attesting Officer*      *Commissioner of Patents and Trademarks*